(12) United States Patent
Zen (10) Patent No.: US 9,325,881 B2
(45) Date of Patent: Apr. 26, 2016

(54) IMAGING MECHANISM AND ENDOSCOPE APPARATUS

(71) Applicant: Olympus Corporation, Tokyo (JP)

(72) Inventor: Kenichi Zen, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 509 days.

(21) Appl. No.: 13/716,494

(22) Filed: Dec. 17, 2012

(65) Prior Publication Data

US 2013/0169777 A1    Jul. 4, 2013

(30) Foreign Application Priority Data

Dec. 28, 2011    (JP) ................ 2011-289349

(51) Int. Cl.
 *H04N 7/18*    (2006.01)
 *H04N 5/225*    (2006.01)
 *A61B 1/05*    (2006.01)

(52) U.S. Cl.
 CPC .............. *H04N 5/2251* (2013.01); *A61B 1/051* (2013.01)

(58) Field of Classification Search
 None
 See application file for complete search history.

(56) References Cited

U.S. PATENT DOCUMENTS

| 6,142,930 | A | 11/2000 | Ito et al. |
| 6,567,115 | B1 | 5/2003 | Miyashita et al. |
| 2002/0080233 | A1 | 6/2002 | Irion et al. |
| 2004/0227068 | A1* | 11/2004 | Raynor et al. ............... 250/239 |
| 2007/0177008 | A1* | 8/2007 | Bayer et al. ..................... 348/65 |
| 2009/0021618 | A1 | 1/2009 | Schwarz et al. |
| 2009/0027491 | A1 | 1/2009 | Irion et al. |
| 2012/0169922 | A1* | 7/2012 | Wang et al. .................... 348/374 |

FOREIGN PATENT DOCUMENTS

| JP | 11326787 A | 11/1999 |
| JP | 2006-068058 A | 3/2006 |

OTHER PUBLICATIONS

Extended European Search Report (EESR) dated Mar. 12, 2013 (in English) issued in counterpart European Application No. 12008318.3.

Japanese Office Action (and English translation thereof) dated Nov. 4, 2015, issued in counterpart Japanese Application No. 2011-289349.

* cited by examiner

*Primary Examiner* — Eileen Adams
(74) *Attorney, Agent, or Firm* — Holtz, Holtz & Volek PC (57) ABSTRACT

An imaging mechanism and an endoscope apparatus include: an image sensor including a sensor face and a plurality of input/output leads, a holding member having a sensor contact face, a circuit board that is secured to an outer face of an opposite side of the holding member to the sensor contact face, and a contact-point part disposed on a side face of the circuit board intersecting with a mount face, and in a region where the outline of the circuit board is inside the outline of the holding member. At least one of the holding member and the circuit board includes a relay wiring part which the contact-point part and at least one of the input/output leads are electrically connected to.

8 Claims, 4 Drawing Sheets

IMAGING MECHANISM AND ENDOSCOPE APPARATUS

BACKGROUND OF THE INVENTION

1. Field of the Invention

The present invention relates to an imaging mechanism and an endoscope apparatus. The present application claims priority on Japanese Patent Application No. 2011-289349, filed on Dec. 28, 2011, the content of which is incorporated herein by reference.

2. Description of the Related Art

Conventionally, there is a known method of inserting an endoscope apparatus into the internal part and the like of an observation object and thereby observing it. For example, an endoscope apparatus including an elongated insertion part having a distal end and a proximal end, and an imaging mechanism for taking an image of a target disposed at the distal end of the insertion part, is known.

As an example of such an imaging mechanism, Japanese Unexamined Patent Application, First Publication No. 2006-68058 discloses a distal-end part of an electronic endoscope. In the electronic endoscope disclosed in Japanese Unexamined Patent Application, First Publication No. 2006-68058, a base with a solid-state imaging device (image sensor) mounted thereon and a signal line electrically connected to the image sensor are sealed in resin at the distal-end part.

The resin at the distal-end part of the electronic endoscope disclosed in Japanese Unexamined Patent Application, First Publication No. 2006-68058 is hard. Consequently, the section where the resin is provided is a hard part with poor flexibility. The hard part mentioned above is the section from the tips of signal lines electrically connected to the image sensor to the section where the signal lines are bundled together.

SUMMARY OF THE INVENTION

According to a first aspect of the present invention, an imaging mechanism includes: an image sensor, a holding member, a circuit board and contact-point part. The image sensor includes a sensor face whereon a plurality of light-receiving elements and a plurality of input/output leads are arranged. The holding member has a sensor contact face that contacts a face of the image sensor that is on an opposite side to the side where the sensor face is provided. The circuit board is secured to an outer face of an opposite side of the holding member to the sensor contact face, and includes a mount face parallel with the sensor face, at least one part of the outline of the circuit board when seen from a direction perpendicular to the mount face being inside the outline of the holding member. The contact-point part is disposed on a side face of the circuit board intersecting with the mount face, and in a region where the outline of the circuit board is inside the outline of the holding member. At least one of the holding member and the circuit board includes a relay wiring part to which the contact-point part is electrically connected, and to which at least one of the input/output leads is electrically connected.

According to a second aspect of the present invention, the imaging mechanism includes a first wiring for transmitting an electrical power or an electrical signal to the image sensor that is connected to the contact-point part. A second contact-point part is provided on a different side face to the face whereon the contact-point part is disposed, and a second wiring for transmitting electrical power or an electrical signal to the image sensor and at least another one of the input/output leads being connected to the second contact-point part. At least one of the first wirings has a greater outer diameter than that of the second wiring.

According to a third aspect of the present invention, a second contact-point part is provided on a different side face to the face whereon the contact-point part is disposed, a second wiring for transmitting an electrical power or an electrical signal to the image sensor and at least another one of the input/output leads being connected to the second contact-point part. A third contact-point part being different to the contact-point part is disposed in the region. The third contact-point part is connected to a conductor pattern provided on the circuit board. The third contact-point part is electrically connected to an electronic component mounted on the circuit board. A third wiring for transmitting electrical power or an electrical signal to at least one of the electronic component and the image sensor is electrically and mechanically connected to the third contact-point part.

According to a fourth aspect of the present invention, one or more of the third contact-point parts is provided. At least one of the third wirings connected to the third contact-point parts has a larger outer diameter than that of the second wiring.

According to a fifth aspect of the present invention, an electronic component is mounted on a mount face of the circuit board, and has an outer face parallel with the mount face. A thermally conductive insulating cover is secured to the circuit board and covers the electronic component. A thermally conductive sheet with thermal conductivity and insulating characteristics is inserted between the outer face of the electronic component and the cover.

According to a sixth aspect of the present invention, length of the cover measured around an axis perpendicular to the mount face at the ends of sides far from the mount face is shorter than the length measured at the ends of sides near the mount face.

According to a seventh aspect of the present invention, the holding member has a lead contact face that intersects the sensor contact face among the outer faces of the holding member. The input/output leads protrude from the sensor face in the direction of the sensor contact face, bend in the direction of the lead contact face, and extend toward the lead contact face. A conductor pattern is formed on the lead contact face in correspondence with the pitch of the input/output leads, and the input/output leads are electrically and mechanically connected to the conductor pattern.

According to an eighth aspect of the present invention, an endoscope apparatus includes: an elongated insertion part having a distal end and a proximal end, the imaging mechanism according to any one of the first to the seventh aspects, and an operation portion provided at the proximal end of the insertion part. The imaging mechanism is disposed at the distal end of the insertion part and used for taking an image of an observation object.

According to a ninth aspect of the present invention, the endoscope apparatus includes: an elongated insertion part having a distal end and a proximal end; an imaging mechanism according to the fifth or sixth aspect; and a main-unit part provided at the proximal end of the insertion part. The imaging mechanism is disposed at the distal end of the insertion part and used for taking an image of an observation object. A metal wire is provided in an internal part of the insertion part, a distal end of the metal wire being thermally connected to the cover.

DETAILED DESCRIPTION OF THE INVENTION

Figure 1:
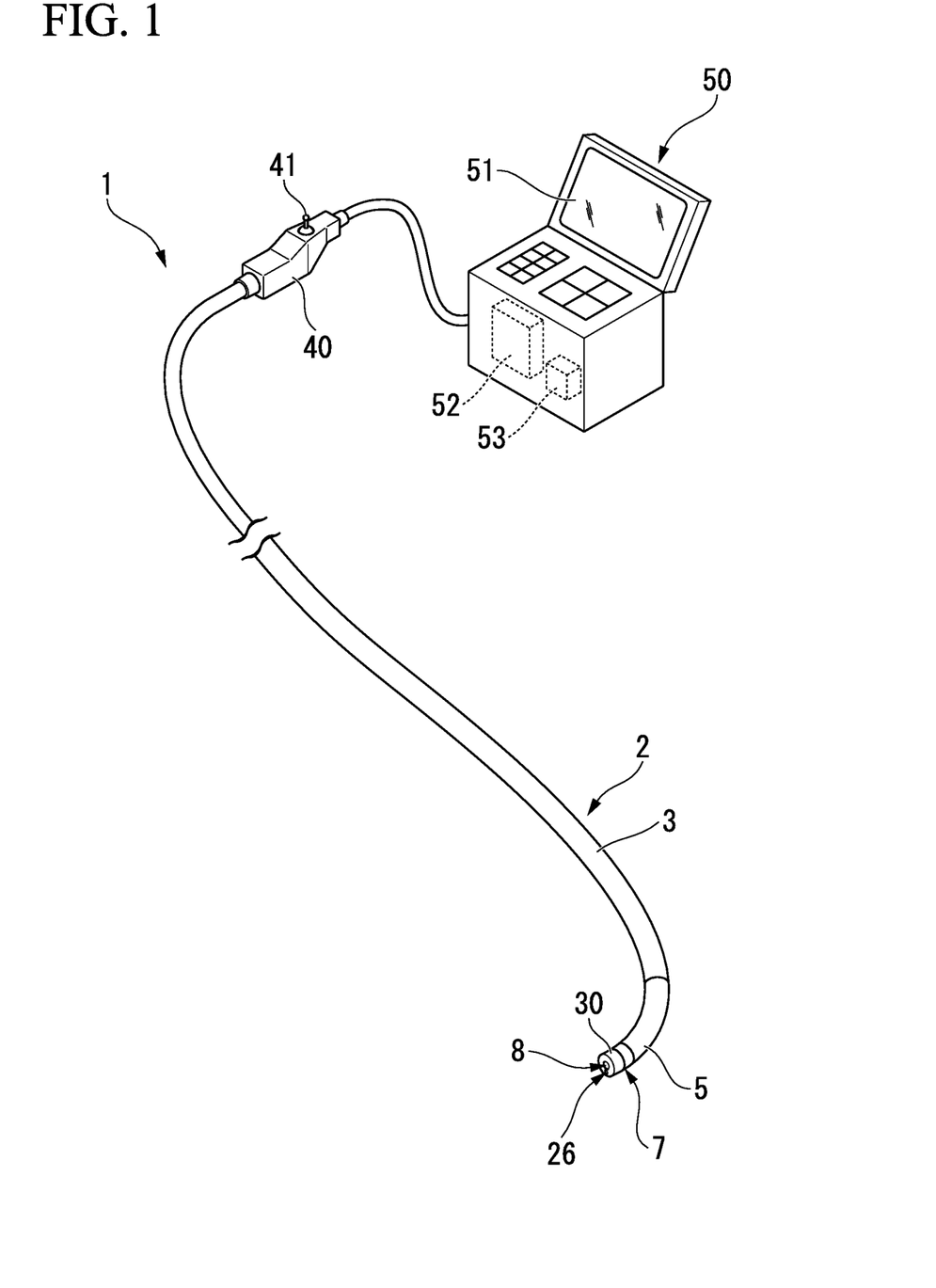
FIG. 1 is an overall view of an endoscope apparatus of one embodiment of the present invention.
Figure 2:
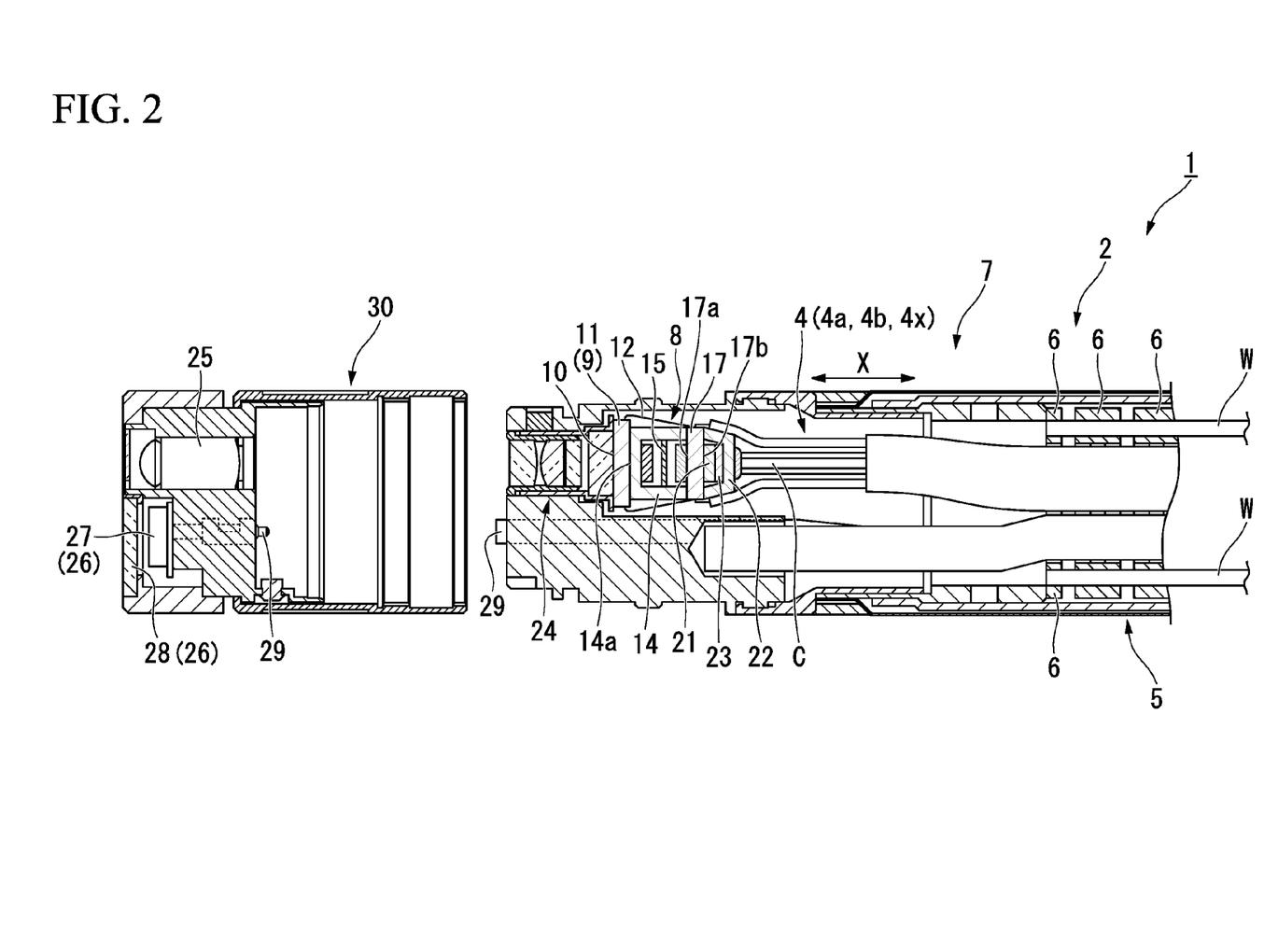
FIG. 2 is a cross-sectional view of a distal-end section of an insertion part in the endoscope apparatus.
Figure 3:
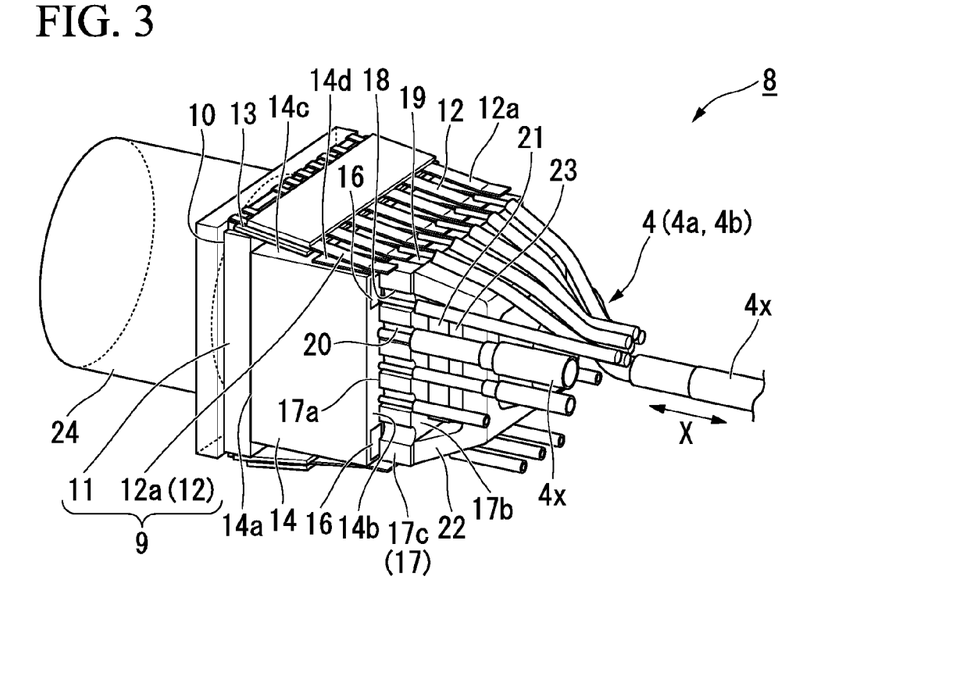
FIG. 3 is a perspective view of an imaging mechanism provided in the endoscope apparatus.
Figure 4:
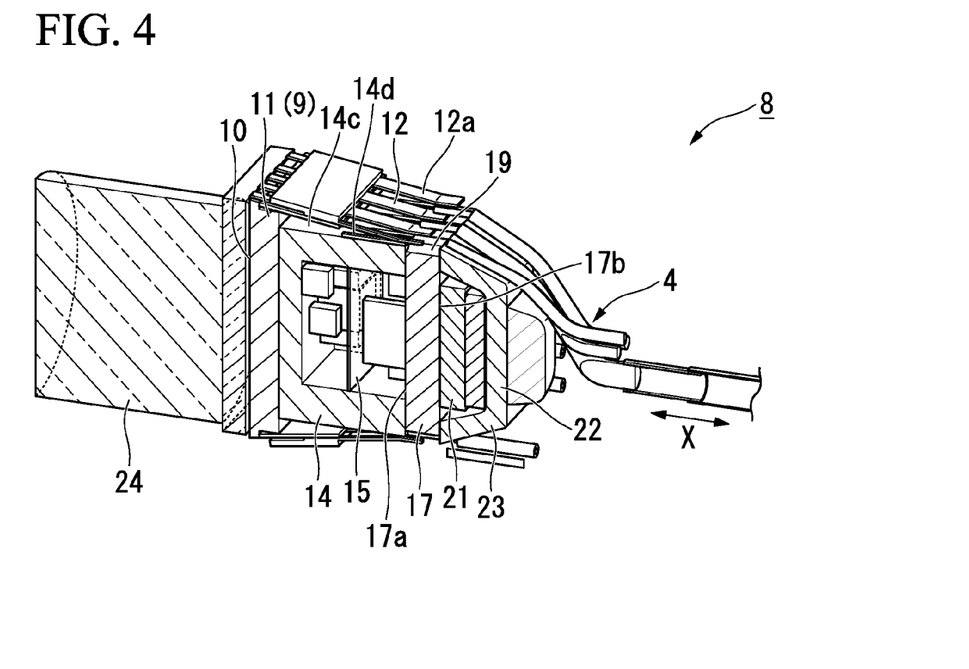
FIG. 4 is a cross-sectional view of the imaging mechanism.
Figure 5:
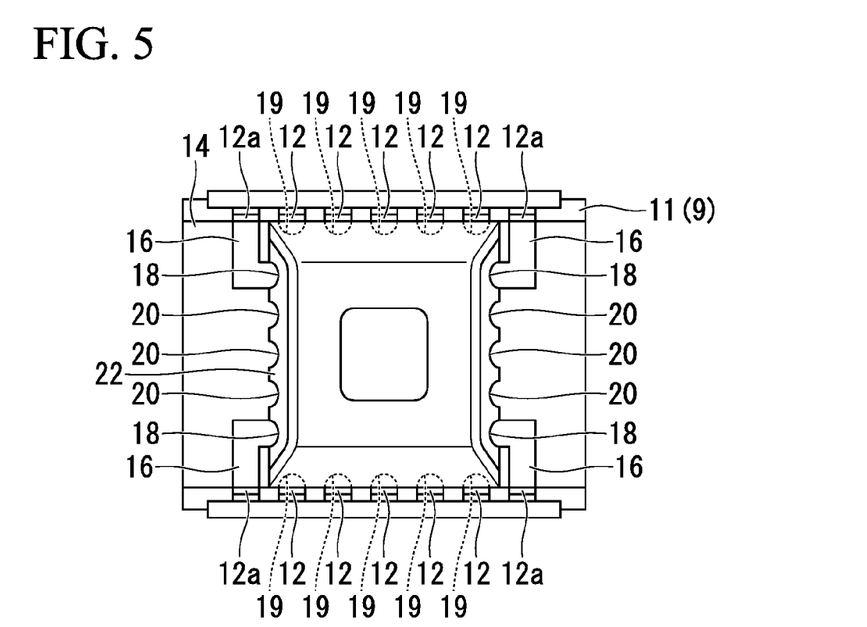
FIG. 5 is a view of the imaging mechanism when seen from the proximal end toward the distal end.
Figure 6:
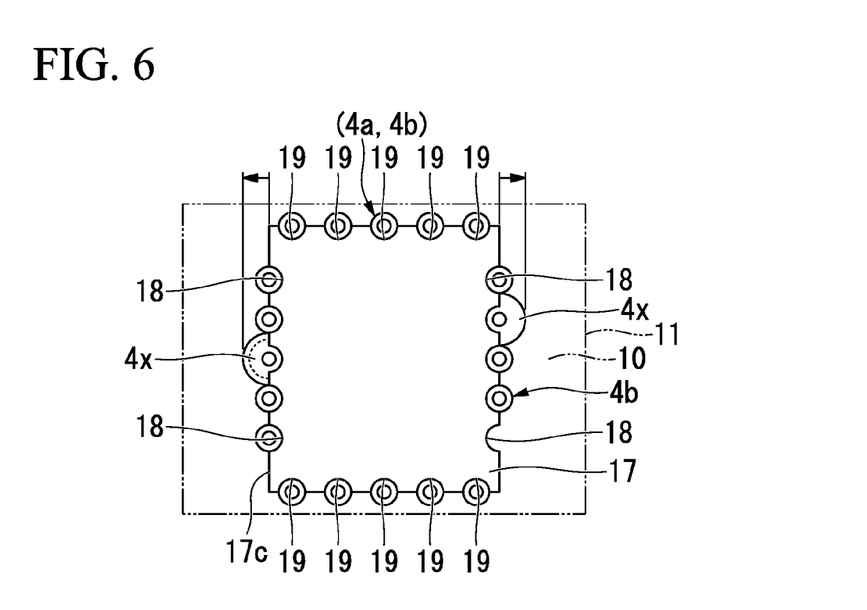
FIG. 6 is a view of the imaging mechanism when seen from the distal end toward the proximal end.

An imaging mechanism 8 and an endoscope apparatus 1 of one embodiment of the present invention will be explained. FIG. 1 is an overall view of the endoscope apparatus 1 of the present embodiment. FIG. 2 is a cross-sectional view of a distal-end section of an insertion part in the endoscope apparatus 1. FIG. 3 is a perspective view of an imaging mechanism 8 provided in the endoscope apparatus. FIG. 4 is a cross-sectional view of the imaging mechanism 8. FIG. 5 is a view of the imaging mechanism 8 when it is seen from the proximal end toward the distal end. FIG. 6 is a view of the imaging mechanism 8 when it is seen from the distal end toward the proximal end.

As shown in FIG. 1, the endoscope apparatus 1 includes an elongated insertion part 2 that is inserted from a distal end into an internal part or the like of an observation object, an operation portion 40 provided at a proximal end of the insertion part 2, and a main-unit part 50 that is electrically connected to the operation portion 40 by a cable.

As shown in FIGS. 1 and 2, the insertion part 2 includes a flexible tube part 3, a bending portion 5 provided at the distal end of the flexible tube part 3, and a distal-end configuration part 7 disposed at the distal end of the bending portion 5.

As shown in FIG. 2, the flexible tube part 3 is a cylindrical member having a hollow structure and forming a circular shape in the cross-section of its diameter direction. The flexible tube part 3 internally includes an angle wire W for bending the bending portion 5, and a wiring part 4 for transmitting power and electrical signals to the imaging mechanism 8 and an illuminating mechanism 26 described below, which are provided at the distal-end configuration part 7.

The bending portion 5 has a bendable cylindrical shape, and, when shaped in a straight line, is secured to the flexible tube part 3 such that it is coaxial therewith. The bending portion 5 includes a plurality of joint rings or bender pieces (hereinafter referred to as 'joint rings 6') arranged in its central axis direction. Adjacent joint rings 6 among the plurality of joint rings 6 are connected to each other. The distal end of the angle wire W is connected to the nodal ring 6 that is furthest to the distal-end side of the bending portion 5, and the bending portion 5 is bent by moving the angle wire W in the proximal-end direction.

The distal-end configuration part 7 includes the imaging mechanism 8, an imaging optical system 24 that leads external light to the imaging mechanism 8, and an illuminating mechanism 26 that radiates illuminating light to an observation object. The distal-end configuration part 7 also includes a replaceable cap-shaped optical adaptor 30.

As shown in FIGS. 2 and 3, the imaging mechanism 8 is provided for taking an image of an observation object, and includes an image sensor 9, a holding member 14, a circuit board 17, and a cover 22.

The image sensor 9 includes a sensor unit 11 and input/output leads 12 for inputting and outputting to and from the signal processing circuit. The sensor unit 11 includes a sensor face 10 whereon a plurality of light-receiving elements are arranged in series, and a signal processing circuit (not shown) that reads signals from light-receiving elements of the sensor face 10 and outputs them.

In the embodiment, the sensor unit 11 is shaped like a plate that is rectangular when seen from the direction orthogonal to the sensor face 10. Also, when seen from the direction orthogonal to the sensor face 10, a plurality of input/output leads 12 extend from each of one pair of opposing sides of the sensor unit 11. The sensor face 10 has a rectangular shape with a predetermined aspect ratio of 4:3, 16:9, etc.

In the embodiment, an example is described where the outline of the sensor unit 11 is shaped like a rectangular plate when seen from the direction orthogonal to the sensor face 10. However, the shape of the sensor unit 11 is not limited to this.

In the embodiment, the input/output leads 12 of the image sensor 9 protrude from the sensor face 10 in the direction of a sensor contact face 14a of the holding member 14, are bent in the direction of a lead contact face 14c, and extend toward this lead contact face 14c. Letting the direction in which the input/output leads 12 protrude from the sensor unit 11 as 0 degrees, the input/output leads 12 are bent more than 90 degrees to the proximal-end side. Each input/output lead 12 contacts the circuit board 17, described below. An insulating member 13 is provided between the input/output leads 12 and the sensor unit 11 to keep them insulated from each other.

As shown in FIGS. 3 and 4, the holding member 14 is an insulating member including the sensor contact face 14a that makes contact with a face provided on an opposite side of the image sensor 9 to that of the sensor face 10.

A conductor pattern (not shown) is formed in the holding member 14, and becomes a heat path for heat generated from the image sensor 9 while it is operating.

The holding member 14 has the shape of a box with the sensor contact face 14a as the bottom face. That is, the side of the holding member 14 where the sensor contact face 14a is provided is sealed, and the side opposite to the side where the sensor contact face 14a is provided is open, so that the holding member 14 forms a receptacle shape.

The sensor contact face 14a forms a square shape that is smaller than the outline of the sensor unit 11 when seen from the direction orthogonal to the sensor face 10 of the image sensor 9. The outer-side outline of the holding member 14 substantially forms a rectangular parallelepiped shape.

Some electronic components for controlling the output of an image taken by the image sensor 9 to a control unit 52 described below, and an insulating plate 15 that insulates the electronic components, are provided inside the holding member 14. Inside the holding member 14, components that generate a small amount of heat while operating are disposed on the bottom-face side of the holding member 14 (the distal-end side of the distal-end configuration part 7), and components that generate a large amount of heat while operating are disposed on the open side of the holding member 14 (the proximal-end side of the distal-end configuration part 7). This can greatly suppress the effect of the heat generated by the electronic components on the image sensor 9.

The region around the opening of the holding member 14 is the board contact face 14b, which contacts the circuit board 17 described below. Relay wiring parts 16 are formed on the board contact face 14b, and electrically connect the leads of the image sensor 9 to the terminals of the circuit board 17 described below.

As shown in FIGS. 3 and 5, the relay wiring parts 16 are thin-plate or film-like metal members formed on the outer face of the holding member 14. The relay wiring parts 16 are provided at each of the four corners of the opening in the holding member 14. Of the input/output leads 12 of the image sensor 9, four corner leads 12a extending from the four corners of the image sensor 9 are connected to the relay wiring parts 16.

The relay wiring parts 16 and the corner leads 12a are electrically and mechanically secured by solder.

As shown in FIGS. 3 and 4, the holding member 14 has a lead contact face 14c that intersects the sensor contact face 14a among the outer faces of the holding member 14. A plurality of conductor patterns 14d are formed on the lead contact face 14c in correspondence with the pitch of the plurality of input/output leads 12 of the image sensor 9.

In the embodiment, the conductor patterns 14d have the shape of rectangles that are long in the direction orthogonal to the sensor contact face 14a. In a middle part of the long direction of each conductor pattern 14d, the conductor pattern 14d and the input/output lead 12 are electrically and mechanically connected by solder. The solder sections connecting the conductor patterns 14d and the input/output leads 12 are not shown in FIGS. 3 and 4.

As shown in FIGS. 3 to 5, the circuit board 17 is a plate-shaped member with mount faces 17a and 17b facing parallel with the sensor face 10 of the image sensor 9. One part of a camera control unit for controlling the operation of the image sensor 9 is arranged on the circuit board 17.

As shown in FIG. 4, in the embodiment, the faces of the circuit board 17 in the thick direction are mount faces (mount faces 17a and 17b). Of the electronic components mounted on the circuit board 17, those that generate a relatively large amount of heat are mounted on the mount face 17b, which is on the opposite side to the mount face 17a contacting the opening of the holding member 14.

As shown in FIG. 5, the circuit board 17 has a substantially square-shaped outline when seen from the direction orthogonal to the mount faces 17a and 17b (the direction indicated by letter X in FIG. 4). The length of one side of the circuit board 17 substantially matches the length of the short side of the holding member 14 when seen from the direction orthogonal to the sensor contact face 14a. Contact-point parts 18 where the relay wiring parts 16 are connected, second contact-point parts 19 where the input/output leads 12 of the image sensor 9 are connected, and third contact-point parts 20 where signal wires 4a and imaging-side electrical wires 4b of the wiring part 4 are connected, are provided on the outer face of the circuit board 17 that intersects the two mount faces 17a and 17b (this face is hereinafter termed 'side face 17c').

When seen from the direction orthogonal to the mount faces 17a and 17b (the direction indicated by the letter X in FIG. 4), the contact-point parts 18 are provided on the side face 17c of the circuit board 17 in a region within the outline of the holding member 14. The contact-point parts 18 are made from metal thin film in an indented shape with a groove for fitting the signal wire 4a or the imaging-side electrical wire 4b. The contact-point parts 18 and the relay wiring parts 16 are electrically and mechanically connected by solder or the like. If necessary, the contact-point parts 18 can be electrically connected via internal wiring (not shown) provided inside the circuit board 17 to each electronic circuit mounted on the circuit board 17 (e.g. an electronic component 21) and to electronic components and the like arranged in the holding member 14.

The second contact-point parts 19 are provided at positions corresponding to the positions of the input/output leads 12 of the image sensor 9, and are made from metal thin film in an indented shape with a groove for fitting the input/output leads 12. The second contact-point parts 19 and the input/output leads 12 are electrically and mechanically connected by solder or the like. If necessary, the second contact-point parts 19 can also be connected to internal wiring (not shown) provided inside the circuit board 17. The internal wiring provided inside the circuit board 17 is formed by, for example, a conductor pattern made from a metal thin film. At least one part of each of the second contact-point parts 19 can be a dummy pad that is not connected to the internal wiring of the circuit board 17 or to an electronic circuit mounted on the circuit board 17 (e.g. the electronic component 21).

When seen from the direction orthogonal to the mount faces 17a and 17b (the direction indicated by letter X in FIG. 4), the third contact-point parts 20 are provided on the side face 17c of the circuit board 17 in a region within the outline of the holding member 14, and is arranged between the two contact points 18. The third contact-point parts 20 are electrically connected via internal wiring (not shown) provided inside the circuit board 17 to each electronic circuit mounted on the circuit board 17 (e.g. the electronic component 21).

As shown in FIGS. 3 to 5, the cover 22 is a member for protecting the electronic component 21 mounted on the mount face 17b of the circuit board 17 from external force. The cover 22 also becomes a path for radiating the heat generated from the electronic component 21. The cover 22 is secured to the mount face 17b of the circuit board 17 such that it is disposed along the outer peripheral section of the mount face 17b of the circuit board 17. The material used for the cover 22 is preferably one that does not easily deform due to external force, e.g. ceramics, etc.

The shape of the cover 22 is such that, when its length is measured around an axis perpendicular to the mount faces 17a and 17b, the length of the cover 22 at the ends of the sides far from the mount faces 17a and 17b is shorter than the length of the cover 22 at the ends of the sides near the mount faces 17a and 17b. In other words, in the embodiment, the diameter of the cover 22 gradually decreases toward the proximal-end side of the distal-end configuration part 7. Some of the wires constituting the wiring part 4 (e.g. the signal wires 4a and the imaging-side electrical wires 4b) are disposed on the outer face of the cover 22. The wiring part 4 extends along the outer face of the cover 22 to the proximal-end side, where it is more bundled than at the cover 22.

In the embodiment, the cover 22 has the shape of a truncated pyramid with the face contacting the mount face 17b as its bottom face, and parts of its side faces are open.

The cover 22 has a thermally conductive sheet 23 with high thermal conductivity, which adheres to the electronic component 21. When the cover 22 is secured to the circuit board 17, the thermally conductive sheet 23 is pushed by both the electronic component 21 and the inner face of the cover 22. The cover 22 and the thermally conductive sheet 23 are made from an insulating material. Preferably, the thermally conductive sheet 23 has elasticity.

As shown in FIG. 2, the distal end of a metal wire C for radiating heat generated from the electronic component 21 mounted on the circuit board 17 is connected to the outer face of the cover 22 such that the heat is transmitted favorably. The metal wire C is formed from a wire of braided or twisted metal.

Part of the wiring part 4 (e.g. the signal wires 4a and the imaging-side electrical wires 4b) can also be used as the metal wire C. For example, when the signal wire 4a includes a noise-reducing shield wire, this shield wire can be used to disperse heat from the cover 22.

In the wiring part 4 (e.g. the signal wires 4a and the imaging-side electrical wires 4b) connected to the imaging mechanism 8, wires that need not be directly connected to the input/output leads 12 of the image sensor 9 are connected to the third contact-point parts 20.

The signal wires 4a and the imaging-side electrical wires 4b for connection to the third contact-point parts 20 are selected by prioritizing them based on their outer diameters. That is, the signal wires 4a and the imaging-side electrical wires 4b for connection to the third contact-point parts 20 are selected in order from the one with the thickest diameter and connected to the third contact-point parts 20. The configuration of the internal wiring of the circuit board 17 is determined in accordance with the wires connected to the third contact-point parts 20. The outer diameters of the wires connected to the third contact-point parts 20 are determined depending on the outer diameters of various constitutive elements such as the core, a covering, and a shield. For example, there are cases where the core of the signal wire 4a for transmitting a signal of the image taken by the imaging mechanism 8 is covered with a shield to prevent noise from infiltrating the signal, and its outer diameter will thus tend to be greater than other signal wires 4a that include only a core and a covering. For that reason, it is particularly preferable to connect the signal wires 4a to the third contact-point parts 20.

In the third contact-point parts 20, the signal wires 4a and the imaging-side electrical wires 4b to be connected to the third contact-point parts 20 are arranged such that they do not stick out from the outline of the image sensor 9 when seen from a direction perpendicular to the mount faces 17a and 17b of the circuit board 17. Similarly, in the second contact-point parts 19 and the contact points 18, the signal wires 4a and the imaging-side electrical wires 4b are arranged such that they do not stick out from the outline of the image sensor 9 when seen from a direction perpendicular to the mount faces 17a and 17b of the circuit board 17.

The signal wires 4a and the imaging-side electrical wires 4b to be connected to the imaging mechanism 8, extend along the outer face of the cover 22 to the flexible tube part 3 side, where they are bundled together and inserted into the flexible tube part 3. When seen from a direction perpendicular to the mount faces 17a and 17b of the circuit board 17, the signal wires 4a and the imaging-side electrical wires 4b to be connected to the imaging mechanism 8 are within the inside region of the outline of the image sensor 9. Each of the signal wires 4a and the imaging-side electrical wires 4b to be connected to the imaging mechanism 8 is secured by an adhesive or the like from the circuit board 17 as far as the bundled section mentioned above, and is arranged such that it does not become disconnected from the circuit board 17 or break due to external force.

As shown in FIG. 2, the optical axis of the imaging optical system 24 is positioned such that the center of the sensor face 10 of the image sensor 9 intersects the sensor face 10 at a right angle. There are no particular limitations on the configuration of the imaging optical system 24, and it can include a zoom mechanism or the like. The imaging optical system 24 can be combined with an additional objective optical system 25 for modifying the optical characteristics. For example, in this embodiment, the additional objective optical system 25 is provided in the optical adaptor 30.

The illuminating mechanism 26 includes a light source 27 provided inside the optical adaptor 30, an illumination optical system 28 for controlling the distribution of light generated from the light source 27, the illumination optical system 28 being provided in the optical adaptor 30, and an illumination power line 29 that supplies electrical power to the light source 27. A light-emitting diode or such like can, for example, be used as the light source 27. The illumination power line 29 extends through the internal part of the flexible tube part 3 to the internal part of the operation portion 40, and connects to a control unit 52 described below.

As shown in FIG. 1, the operation portion 40 is provided with a joystick 41 which a user manipulates to input the bend direction for bending the bending portion 5. In the endoscope apparatus 1 of this embodiment, when the joystick 41 is tilted with respect to a predetermined intermediate position, that direction is input to the main-unit part 50 as the direction for bending the bending portion 5. The main unit bends the bending portion 5 based on the input from the joystick 41.

The main-unit part 50 includes a display unit 51, a control unit 52, and a power unit 53.

The display unit 51 is a device for displaying an image taken by the imaging mechanism 8, and includes, for example, a liquid crystal display panel and a display control circuit.

The control unit 52 includes various types of electronic components for controlling the operations of the imaging mechanism 8, the illuminating mechanism 26, and the display unit 51.

The power unit 53 supplies power for driving the imaging mechanism 8, the illuminating mechanism 26, the display unit 51, and the control unit 52. In this embodiment, a battery and a power control circuit are provided inside the main-unit part 50. Instead of providing the battery and the power control circuit inside the main-unit part 50, or in addition to the battery and the power control circuit, a power unit for using a commercial power supply to drive the endoscope apparatus 1 can be provided in the main unit.

Subsequently, operations of the imaging mechanism 8 and the endoscope apparatus 1 will be explained.

The insertion part 2 of the endoscope apparatus 1 is inserted into an internal part or the like of an observation object, and preferably has a small diameter. The space for housing the internal structural element of the insertion part 2 is therefore limited. For example, the imaging mechanism 8 and the illuminating mechanism 26 must be housed together in a limited space in the distal-end configuration part 7. To protect the imaging mechanism 8 and the illuminating mechanism 26 from external forces, the distal-end configuration part 7 is hard. When the distal-end configuration part 7 is long in the central axis direction, if an observation object attempts to bend with a small radius of curvature in a narrow region, the distal end of the insertion part 2 will fail to bend and will collide, making it difficult to guide the distal end of the insertion part 2. In the embodiment, the sections where the signal wires 4a and the imaging-side electrical wires 4b of the imaging mechanism 8 are secured together also have little flexibility, and these hard configuration sections produce a hard part at the distal-end section of the insertion part 2.

As shown in FIGS. 3 and 6, in the embodiment, those of the signal wires 4a and the imaging-side electrical wires 4b with a thick outer diameter (e.g. signal wires 4x and 4y in FIG. 6) are connected on a priority basis to the third contact-point parts 20, and are arranged on the inner side of the outline of the image sensor 9 when seen from the central axis direction of the distal-end configuration part 7.

Moreover, since the wires with a thick outer diameter are provided near the center of the circuit board 17 when seen from the thick direction of the circuit board 17, when they are bundled together with the other wires, even if the length of the section where the signal wires 4a and the imaging-side electrical wires 4b of the imaging mechanism 8 are secured together in the central axis direction of the distal-end configuration part 7 is reduced, the thick wires need only be bent by a small amount. As a result, the length of the hard part can be reduced, while the burden on the thick wires due to bending them is kept small.

When the image sensor 9 includes a great many light-receiving elements, in comparison with when the image sensor has few light-receiving elements, the signals flowing in the signal wires 4a have higher frequencies and the effects of noise on the signals is liable to be considerable. Therefore, when using such an image sensor 9, the outer diameter of the signal wires 4a is liable to become thick due to a shield being provided to the signal wires 4a, each signal wire 4a and a ground wire being configured as a twisted pair, etc. Furthermore, when the image sensor 9 has a great many light-receiving elements, it tends to become large. If the signal wires 4a stick out from the outline of the image sensor 9 when seen from the direction perpendicular to the sensor face 10 of the image sensor 9, there is a possibility that the diameter of the distal-end configuration part 7 will become large.

In contrast, as shown in FIG. 6, when the imaging mechanism 8 of the embodiment is seen from the direction perpendicular to the sensor face 10 of the image sensor 9 (i.e. the central axis direction of the distal-end configuration part 7), the signal wires 4a and the imaging-side electrical wires 4b are inside the outline of the image sensor 9. Thus the size of the imaging mechanism 8 when seen from the direction perpendicular to the sensor face 10 of the image sensor 9 is defined by the size of the image sensor 9. This prevents the diameter of the distal-end configuration part 7 from being greatly increased due to the signal wires 4a and the imaging-side electrical wires 4b, connected to the imaging mechanism 8, sticking out from the outline of the image sensor 9.

While the imaging mechanism 8 is operating, heat generated by the image sensor 9 and other electronic components can sometimes result in thermal noise due to dark current to the image sensor 9. In the embodiment, heat generated by the image sensor 9 is dispersed via the holding member 14, the circuit board 17, the thermally conductive sheet 23, and the cover 22 shown in FIG. 4 to the metal wire C (see FIG. 2).

This can reduce noise in the image due to the rising temperature of the image sensor 9. Especially, the image sensor 9 generates a large amount of heat when it includes a great many light-receiving elements, and when the operating frequency of the signal processing circuit increases.

This embodiment includes a heat-radiation path provided in a straight line from the distal end of the insertion part 2 to the proximal end, and can thus reduce the accumulation of heat from the image sensor 9 and other electronic components arranged at the distal end of the insertion part 2. Therefore, deterioration in the quality of the image taken by the image sensor 9 can be suppressed.

As described above, according to the imaging mechanism 8 and the endoscope apparatus 1 of the embodiment, a large image sensor 9 can be mounted while suppressing an increase in the length of the hard part of the insertion part 2. As a result, even if a high-quality image sensor 9 is mounted, the insertion part 2 can be prevented from becoming large.

When an image sensor similar to conventional types is mounted, the length of the hard part can be reduced.

Since the path favorably shifts heat generated by the image sensor 9 to the proximal-end side of the insertion part 2, the effects of noise on the image sensor 9 can be suppressed to a low level, enabling a high-quality image to be taken.

While an embodiment of the invention has been described in detail with reference to the drawings, the specific configuration is not limited to this embodiment, it being possible to make various design modifications and the like without deviating from the main points of the invention.

For example, grease with high thermal conductivity can be provided instead of the thermally conductive sheet 23.

The sensor contact face of the holding member can have a rectangular shape (including a substantially rectangular shape) that matches the outline of the sensor main unit when seen from the direction orthogonal to the sensor face of the image sensor.

The relay wiring parts can be provided on faces other than the board contact face. Also, the relay wiring parts can be connected to the conductor pattern formed on the lead contact face of the holding member.

The relay wiring parts can be formed on side faces of the circuit board.

Moreover, the relay wiring parts can be formed on both the holding member and the circuit board.

In that case, the relay wiring part formed on the holding member and the relay wiring part formed on the circuit board are provided in a state of mutual electrical conduction.

Design modifications and the like to the embodiment of the invention are not limited to those mentioned above. The invention is not to be considered as being limited by the foregoing description, and is only limited by the scope of the appended claims.

What is claimed is:

1. An imaging mechanism comprising:
   an image sensor including a sensor face whereon a plurality of light-receiving elements are arranged, and a plurality of input/output leads;
   a holding member having a sensor contact face that contacts a face of the image sensor that is on an opposite side to the side where the sensor face is provided;
   a circuit board that is secured to an outer face of an opposite side of the holding member to the sensor contact face, and includes a mount face parallel with the sensor face, at least one part of the outline of the circuit board when seen from a direction perpendicular to the mount face being inside the outline of the holding member; and
   a contact-point part disposed on a side face of the circuit board intersecting with the mount face, and in a region where the outline of the circuit board is inside the outline of the holding member;
   wherein:
   at least one of the holding member and the circuit board includes a relay wiring part to which the contact-point part is electrically connected, and to which at least one of the input/output leads is electrically connected;
   a second contact-point part is provided on a different side face to the face whereon the contact-point part is disposed, a second wiring for transmitting an electrical power or an electrical signal to the image sensor and at least another one of the input/output leads being connected to the second contact-point part;
   a third contact-point part different from the contact-point part is disposed in the region;
   the third contact-point part is connected to a conductor pattern provided on the circuit board, and is electrically connected to an electronic component mounted on the circuit board; and
   a third wiring for transmitting electrical power or an electrical signal to at least one of the electronic component and the image sensor is electrically and mechanically connected to the third contact-point part.

2. The imaging mechanism according to claim 1, wherein:
   one or more of the third contact-point parts is provided; and
   at least one of the third wirings connected to the third contact-point parts has a larger outer diameter than an outer diameter of the second wiring.

3. The imaging mechanism according to claim 1, wherein:
the electronic component is mounted on a mount face of the circuit board, and has an outer face parallel with the mount face;
a thermally conductive insulating cover is secured to the circuit board and covers the electronic component; and
a thermally conductive sheet with thermal conductivity and insulating characteristics is inserted between the outer face of the electronic component and the cover.

4. An imaging mechanism comprising:
an image sensor including a sensor face whereon a plurality of light-receiving elements are arranged, and a plurality of input/output leads;
a holding member having a sensor contact face that contacts a face of the image sensor that is on an opposite side to the side where the sensor face is provided;
a circuit board that is secured to an outer face of an opposite side of the holding member to the sensor contact face, and includes a mount face parallel with the sensor face, at least one part of the outline of the circuit board when seen from a direction perpendicular to the mount face being inside the outline of the holding member; and
a contact-point part disposed on a side face of the circuit board intersecting with the mount face, and in a region where the outline of the circuit board is inside the outline of the holding member;
wherein:
at least one of the holding member and the circuit board includes a relay wiring part to which the contact-point part is electrically connected, and to which at least one of the input/output leads is electrically connected;
an electronic component is mounted on a mount face of the circuit board, and has an outer face parallel with the mount face;
a thermally conductive insulating cover is secured to the circuit board and covers the electronic component;
a thermally conductive sheet with thermal conductivity and insulating characteristics is inserted between the outer face of the electronic component and the cover; and
a length of the cover measured around an axis perpendicular to the mount face at the ends of sides far from the mount face is shorter than the length measured at the ends of sides near the mount face.

5. An imaging mechanism comprising:
an image sensor including a sensor face whereon a plurality of light-receiving elements are arranged, and a plurality of input/output leads;
a holding member having a sensor contact face that contacts a face of the image sensor that is on an opposite side to the side where the sensor face is provided;
a circuit board that is secured to an outer face of an opposite side of the holding member to the sensor contact face, and includes a mount face parallel with the sensor face, at least one part of the outline of the circuit board when seen from a direction perpendicular to the mount face being inside the outline of the holding member; and
a contact-point part disposed on a side face of the circuit board intersecting with the mount face, and in a region where the outline of the circuit board is inside the outline of the holding member;
wherein:
at least one of the holding member and the circuit board includes a relay wiring part to which the contact-point part is electrically connected, and to which at least one of the input/output leads is electrically connected;
the holding member has a lead contact face that intersects the sensor contact face among the outer faces of the holding member;
the input/output leads protrude from the sensor face in the direction of the sensor contact face, bend in the direction of the lead contact face, and extend toward the lead contact face; and
a conductor pattern is formed on the lead contact face in correspondence with the pitch of the input/output leads, and the input/output leads are electrically and mechanically connected to the conductor pattern.

6. An endoscope apparatus comprising:
an elongated insertion part having a distal end and a proximal end;
an imaging mechanism disposed at the distal end of the insertion part and used for taking an image of an observation object; and
an operation portion provided at the proximal end of the insertion part;
wherein the imaging mechanism comprises:
an image sensor including a sensor face whereon a plurality of light-receiving elements are arranged, and a plurality of input/output leads;
a holding member having a sensor contact face that contacts a face of the image sensor that is on an opposite side to the side where the sensor face is provided;
a circuit board that is secured to an outer face of an opposite side of the holding member to the sensor contact face, and includes a mount face parallel with the sensor face, at least one part of the outline of the circuit board when seen from a direction perpendicular to the mount face being inside the outline of the holding member; and
a contact-point part disposed on a side face of the circuit board intersecting with the mount face, and in a region where the outline of the circuit board is inside the outline of the holding member; and
wherein:
at least one of the holding member and the circuit board includes a relay wiring part to which the contact-point part is electrically connected, and to which at least one of the input/output leads is electrically connected;
a second contact-point part is provided on a different side face to the face whereon the contact-point part is disposed, a second wiring for transmitting an electrical power or an electrical signal to the image sensor and at least another one of the input/output leads being connected to the second contact-point part;
a third contact-point part different from the contact-point part is disposed in the region;
the third contact-point part is connected to a conductor pattern provided on the circuit board, and is electrically connected to an electronic component mounted on the circuit board; and
a third wiring for transmitting electrical power or an electrical signal to at least one of the electronic component and the image sensor is electrically and mechanically connected to the third contact-point part.

7. An endoscope apparatus comprising:
an elongated insertion part having a distal end and a proximal end;
an imaging mechanism disposed at the distal end of the insertion part and being used for taking an image of an observation object;
a main-unit part provided at the proximal end of the insertion part; and a metal wire provided in an internal part of the insertion part;

wherein the imaging mechanism comprises:

an image sensor including a sensor face whereon a plurality of light-receiving elements are arranged, and a plurality of input/output leads;

a holding member having a sensor contact face that contacts a face of the image sensor that is on an opposite side to the side where the sensor face is provided;

a circuit board that is secured to an outer face of an opposite side of the holding member to the sensor contact face, and includes a mount face parallel with the sensor face, at least one part of the outline of the circuit board when seen from a direction perpendicular to the mount face being inside the outline of the holding member; and a contact-point part disposed on a side face of the circuit board intersecting with the mount face, and in a region where the outline of the circuit board is inside the outline of the holding member; and wherein:

at least one of the holding member and the circuit board includes a relay wiring part to which the contact-point part is electrically connected, and to which at least one of the input/output leads is electrically connected;

an electronic component is mounted on a mount face of the circuit board, and has an outer face parallel with the mount face;

a thermally conductive insulating cover is secured to the circuit board and covers the electronic component;

a thermally conductive sheet with thermal conductivity and insulating characteristics is inserted between the outer face of the electronic component and the cover; and a distal end of the metal wire is thermally connected to the cover.

8. An endoscope apparatus comprising:

an elongated insertion part having a distal end and a proximal end;

an imaging mechanism disposed at the distal end of the insertion part and used for taking an image of an observation object; and an operation portion provided at the proximal end of the insertion part;

wherein the imaging mechanism comprises:

an image sensor including a sensor face whereon a plurality of light-receiving elements are arranged, and a plurality of input/output leads;

a holding member having a sensor contact face that contacts a face of the image sensor that is on an opposite side to the side where the sensor face is provided;

a circuit board that is secured to an outer face of an opposite side of the holding member to the sensor contact face, and includes a mount face parallel with the sensor face, at least one part of the outline of the circuit board when seen from a direction perpendicular to the mount face being inside the outline of the holding member; and a contact-point part disposed on a side face of the circuit board intersecting with the mount face, and in a region where the outline of the circuit board is inside the outline of the holding member; and wherein:

at least one of the holding member and the circuit board includes a relay wiring part; and when the sensor face is viewed from a direction orthogonal to a plane of the sensor face, the relay wiring part is electrically connected to (i) the contact-point part and (ii) a plurality of corner leads among the plurality of input/output leads, the corner leads extending respectively from four corners of the image sensor.

* * * * *